(12) United States Patent
Schader et al.

(10) Patent No.: US 10,940,272 B2
(45) Date of Patent: Mar. 9, 2021

(54) FEEDBACK MECHANISM FOR A DRUG DELIVERY DEVICE

(71) Applicant: Sanofi-Aventis Deutschland GMBH, Frankfurt am Main (DE)

(72) Inventors: Marc Schader, Frankfurt am Main (DE); Winfried Huthmacher, Frankfurt (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 91 days.

(21) Appl. No.: 16/316,733

(22) PCT Filed: Jul. 12, 2017

(86) PCT No.: PCT/EP2017/067505
§ 371 (c)(1),
(2) Date: Jan. 10, 2019

(87) PCT Pub. No.: WO2018/011251
PCT Pub. Date: Jan. 18, 2018

(65) Prior Publication Data
US 2019/0247580 A1 Aug. 15, 2019

(30) Foreign Application Priority Data
Jul. 14, 2016 (EP) .................................. 16179485

(51) Int. Cl.
*A61M 5/315* (2006.01)
*A61M 5/32* (2006.01)

(52) U.S. Cl.
CPC ...... *A61M 5/3157* (2013.01); *A61M 5/31511* (2013.01); *A61M 5/3287* (2013.01); *A61M 5/3204* (2013.01); *A61M 5/326* (2013.01); *A61M 2205/43* (2013.01); *A61M 2205/581* (2013.01)

(58) Field of Classification Search
CPC ........ A61M 2205/43; A61M 2205/581; A61M 5/31511; A61M 5/3157; A61M 5/3204; A61M 5/326; A61M 5/3287
See application file for complete search history.

(56) References Cited

U.S. PATENT DOCUMENTS

| 3,669,111 A | 6/1972 | Dubner |
| 4,865,591 A | 9/1989 | Sams |
| 5,084,017 A | 1/1992 | Maffetone |

(Continued)

FOREIGN PATENT DOCUMENTS

| CN | 104093440 | 10/2014 |
| JP | 2008-167954 | 7/2008 |

(Continued)

OTHER PUBLICATIONS

PCT International Preliminary Report on Patentability in Appln. No. PCT/EP2017/067505, dated Jan. 15, 2019, 9 pages.

(Continued)

*Primary Examiner* — Deanna K Hall
(74) *Attorney, Agent, or Firm* — Fish & Richardson P.C.

(57) ABSTRACT

The present disclosure relates to a feedback mechanism for a drug delivery device, the feedback mechanism comprising a bushing, the bushing comprising a central aperture adapted to accommodate a piston rod, wherein one or more resilient flaps are provided on the bushing, the flaps extending into the central aperture to allow them to engage one or more transversal ribs on the piston rod.

14 Claims, 12 Drawing Sheets

(56) References Cited

U.S. PATENT DOCUMENTS

| | | |
|---|---|---|
| 5,250,030 A | 10/1993 | Corsich |
| 2003/0055386 A1 | 3/2003 | Strauss et al. |
| 2012/0184917 A1 | 7/2012 | Bom |

FOREIGN PATENT DOCUMENTS

| | | |
|---|---|---|
| WO | WO 2009/095735 | 8/2009 |
| WO | WO 2013/034984 | 3/2013 |
| WO | WO 2015/113968 | 8/2015 |
| WO | WO 2016/089871 | 6/2016 |

OTHER PUBLICATIONS

PCT International Search Report and Written Opinion in Appln. No. PCT/EP2017/067505, dated Oct. 17, 2017, 13 pages.

FEEDBACK MECHANISM FOR A DRUG DELIVERY DEVICE

CROSS REFERENCE TO RELATED APPLICATIONS

The present application is a national stage entry of International Patent Application No. PCT/EP2017/067505, filed on Jul. 12, 2017, and claims priority to European Patent Application No. 16179485.4, filed on Jul. 14, 2016, the entire contents of each of which are incorporated herein by reference.

TECHNICAL FIELD

The present disclosure relates to feedback mechanism for a drug delivery device.

BACKGROUND

Administering an injection is a process which presents a number of risks and challenges for users and healthcare professionals, both mental and physical. Drug delivery devices accommodating pre-filled syringes that are filled with a selected dosage of a medicament for administering the medicament to a patient are known in the art.

SUMMARY

A user can be informed about a status (e.g., an end of dose) of a drug delivery device by, for example, a feedback mechanism for the drug delivery device.

The present disclosure describes an improved feedback mechanism for a drug delivery device.

According to the present disclosure, a feedback mechanism for a drug delivery device comprises a bushing, the bushing comprising a central aperture adapted to accommodate a piston rod, wherein one or more resilient flaps are provided on the bushing, the flaps extending into the central aperture to allow them to engage one or more transversal ribs on the piston rod.

During an injection stroke, a syringe may move relative to the piston rod and abut the bushing so that the bushing is moved along the piston rod. During this movement, the flap abuts one of the transversal ribs and is deflected by the transversal rib upon further movement until the flap disengages the transversal rib and relaxes. This may generate an audible and/or tactile feedback indicating the relative position of the piston rod and the bushing and thus also the relative position of the piston rod and the syringe. In an exemplary embodiment, there may be at least two transversal ribs so that the flap, after having disengaged the transversal rib and relaxed, hits a subsequent transversal rib and generates a click sound. By arranging two or more transversal ribs in a sequence, a series of clicks can be generated during the injection stroke.

In an exemplary embodiment, the flaps are formed within a transversal section of the bushing by cut-outs in the transversal section. Thus, the flaps and the transversal section are integrally formed as one part.

In an exemplary embodiment, the flaps are curved. As opposed to straight flaps, this increases the possible total length of the flaps on a limited size transversal section. Longer flaps may deflect easier and have an increased displacement as opposed to shorter flaps.

In an exemplary embodiment, the bushing comprises one or more spline features adapted to engage corresponding spline features in the piston rod to restrain or prevent relative rotation between the piston rod and the bushing. This ensures that the flaps are correctly aligned with the transversal ribs.

In an exemplary embodiment, the spline features comprise one or more radially inward directed protrusions on the bushing adapted to engage longitudinal slots the piston rod, e.g. in at least one longitudinal web of the piston rod.

In an exemplary embodiment, the one or more protrusions are arranged in the transversal section and a recess is provided radially outward of the protrusion in the transversal section. The recess facilitates outward deflection of the protrusion.

The piston rod may comprise a distal end face providing an axial stop for the protrusions so as to limit movement of the piston rod in the proximal direction relative to the bushing. This may be achieved by the longitudinal slots ending at the distal end face and not extending through it.

In an exemplary embodiment, the bushing comprises one or more proximal beams extending from the transversal section in a proximal direction, wherein the one or more protrusions are arranged on an intersection of the proximal beam with the transversal section, wherein in a relaxed state, the proximal beam is inclined outward in the proximal direction thus providing a lead-in for a distal end face of the piston rod during insertion of the piston rod through the central aperture in a distal direction. Once the distal end face has passed beyond the protrusion during this insertion movement, the protrusion relaxes, engages the longitudinal slot and prevents the distal end face from being moved back out of the central aperture in the proximal direction.

In an exemplary embodiment, the one or more proximal beams are integrally formed with the transversal section.

In an exemplary embodiment, the one or more proximal beams may have an arcuate cross section. This increases stability of the bushing and reduces possible distortion thereof.

In an exemplary embodiment, the piston rod comprises a number of longitudinal webs arranged at an angle relative to one another, wherein the one or more transversal ribs are arranged between at least two adjacent ones of these longitudinal webs. This configuration provides the space for the transversal ribs within the piston rod without adding to its diameter and improves the stiffness of the piston rod.

In an exemplary embodiment, the feedback mechanism may be applied in a drug delivery device, comprising:
a body,
a piston rod arranged in the body in a manner to engage a stopper for displacing it within a syringe barrel of a syringe,
wherein the bushing is adapted to engage the syringe during movement of the piston rod relative to the syringe thus also causing movement of the bushing relative to the piston rod.

In an exemplary embodiment, the number and position of the transversal ribs are selected so as to generate at least on click by engaging the one or more protrusions at an end of dose and/or to indicate a start of the injection and/or to indicate an end of one or more predetermined partial doses.

In an exemplary embodiment, the drug delivery device further comprises a container spring arranged over the piston rod between a proximal end face of the piston rod and the transversal section of the bushing. The axial stop thus also serves as a fixation for the container spring to fix it in a pre-load position.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
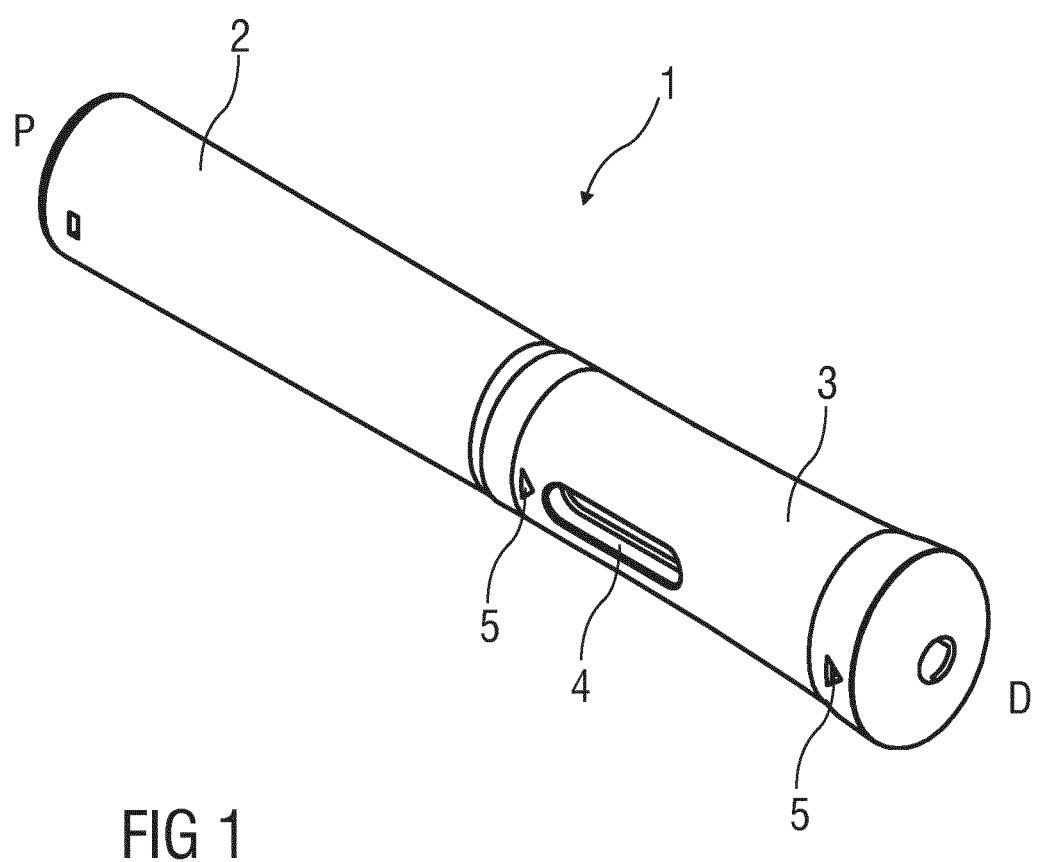
FIG. 1 is a schematic perspective view of an exemplary embodiment of a medicament delivery device prior to use.

FIG. 1 is a perspective view of an exemplary embodiment of a medicament delivery device 1 according to the present disclosure. The medicament delivery device 1 comprises a body 2 which may be generally cylindrical. In an exemplary embodiment, a cap 3 may be removably coupled to the body 2. The cap 3 may include a viewing window 4 (e.g., an opening or a substantially transparent piece of material). The cap 3 may further include one or more indicia 5 for providing a visual and/or tactile indication of use (e.g., which end of the device 1 should be applied to an injection site, etc.). For example, in an exemplary embodiment, the indicia 5 include one or more arrows (painted or embossed) pointing toward a distal end of the device 1.

Figure 2:
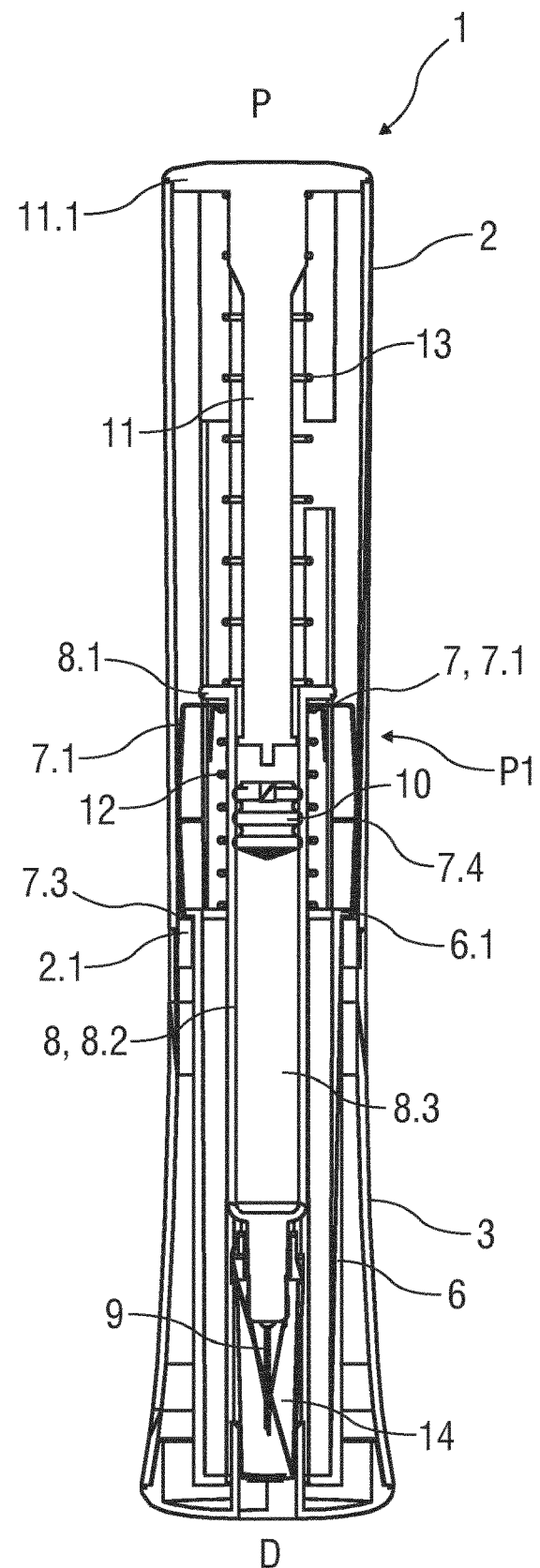
FIG. 2 is a schematic longitudinal section of an exemplary embodiment of a medicament delivery device prior to use.

FIG. 2 is a longitudinal section of an exemplary embodiment of a medicament delivery device 1 according to the present disclosure. A sleeve 6 is slidably coupled to the body 2. For example, the sleeve 6 may be telescoped within the body 2. In an exemplary embodiment, the sleeve 6 comprises one or more lateral sleeve windows 6.2 adapted to axially align with the viewing windows 4 (e.g., an opening or a substantially transparent piece of material) in the cap 3 when the sleeve 6 is in an extended position (as shown in FIG. 2) relative to the body 2.

In an exemplary embodiment, a container carrier 7 slidably disposed in the body 2. The container carrier 7 is adapted to retain a medicament container, e.g., a syringe 8, an ampoule, a cartridge, etc. For example, the syringe 8 includes a syringe barrel 8.2 arranged as a hollow cylinder defining a cavity 8.3 for receiving a medicament. A needle 9 is arranged at a distal end of the syringe barrel 8.2 in a manner to be in fluid communication with the cavity 8.3. A stopper 10 is disposed within the syringe barrel 8.2 for proximally limiting the cavity 8.3. The stopper 10 may be displaced within the syringe barrel 8.2 for ejecting the medicament from the cavity 8.3 through the needle 9.

Figure 3:
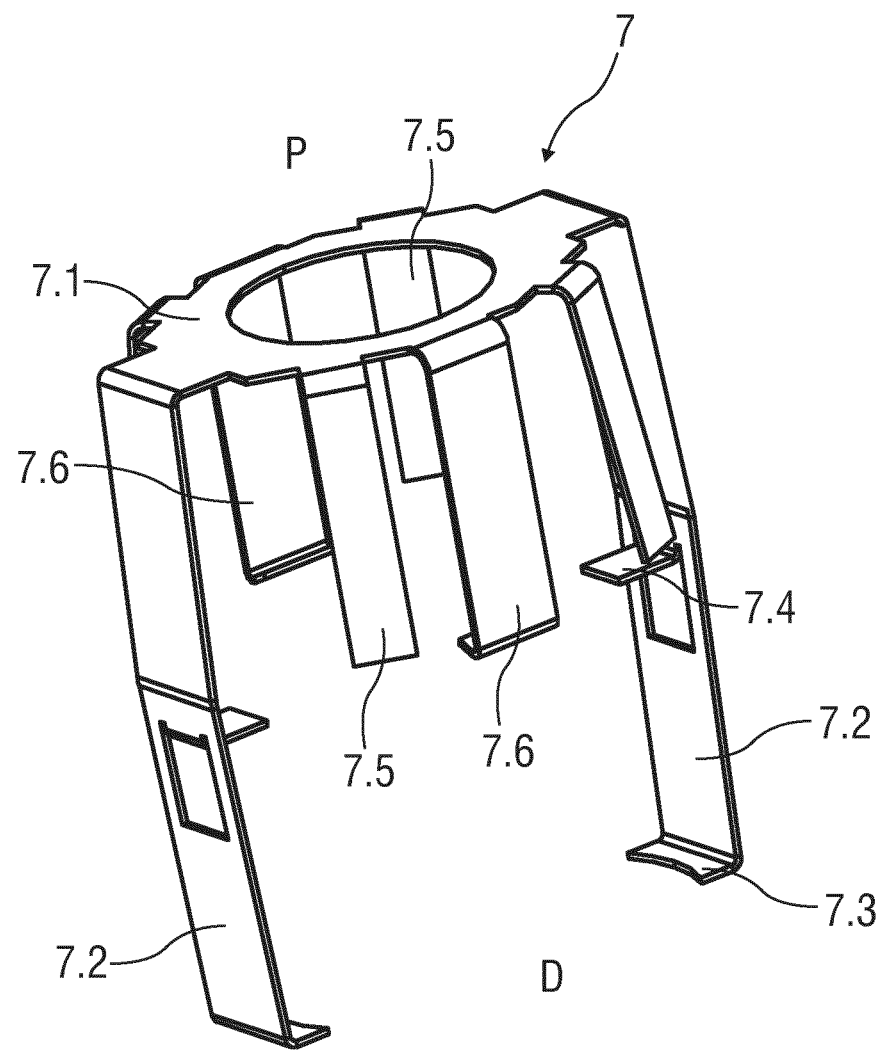
FIG. 3 is a schematic perspective view of an exemplary embodiment of a container carrier according to the present disclosure.

FIG. 3 shows an exemplary embodiment of a container carrier 7 according to the present disclosure. The container carrier 7 comprises a proximal portion 7.1 adapted to engage the medicament container. For example, the proximal portion 7.1 may support a flange 8.1 on a syringe barrel 8.2 of the syringe 8 such that the syringe 8 is prevented from moving in the distal direction D relative to the carrier 7. One or more first legs 7.2 extend distally from the proximal portion 7.1. In an exemplary embodiment, the first leg 7.2 comprises a radially inwardly directed first protrusion 7.3 arranged on a distal end of the first leg 7.2 and a radially inwardly directed second protrusion 7.4 proximal of the first protrusion 7.3. The first protrusion 7.3 and the second protrusion 7.4 are adapted to abut a collar 6.1 on the sleeve 6 for limiting axial movement of the sleeve 6 relative to the carrier 7. The first leg 7.2 is adapted to distally abut a first axial stop 2.1 in the body 2 limiting movement of the carrier 7 in the distal direction relative to the body 2.

Figure 5:
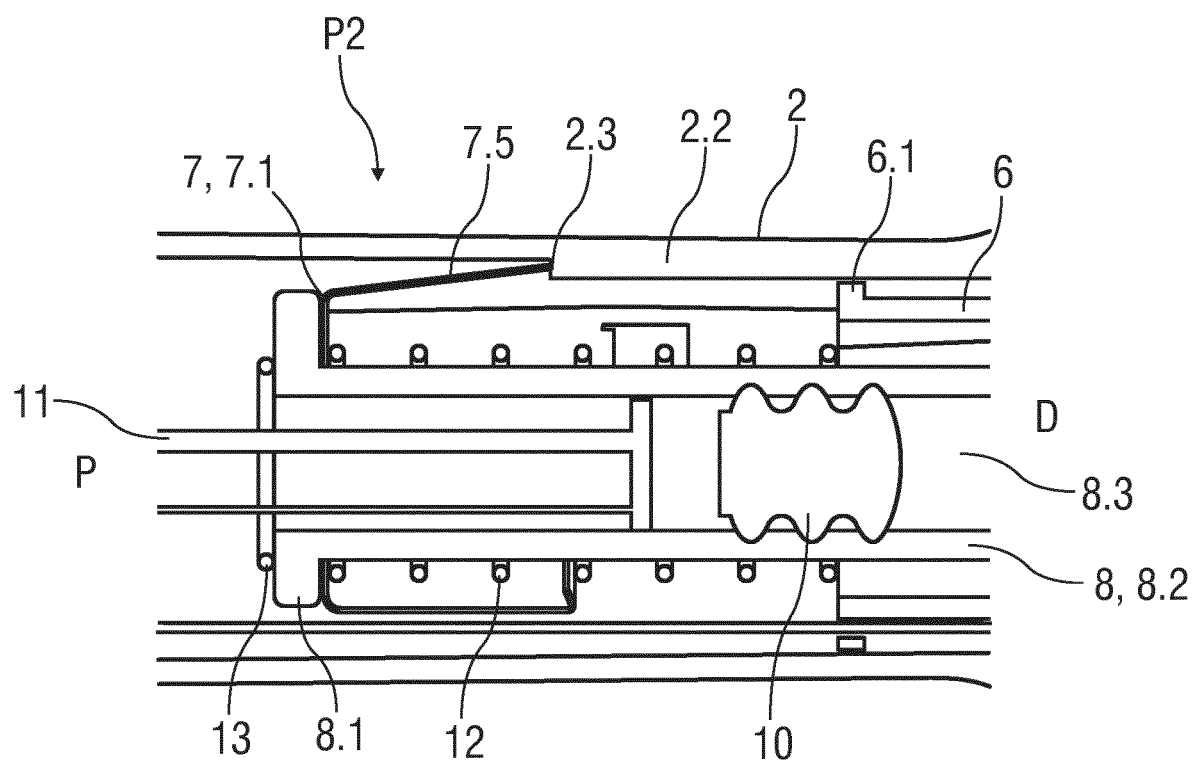
FIG. 5 is a schematic longitudinal detail section of an exemplary embodiment of a medicament delivery device during use.

One or more second legs 7.5 extend distally from the proximal portion 7.1. The second leg 7.5 is biased radially outward. The second leg 7.5 is adapted to engage one or more first ribs 2.2 (e.g., as shown in FIG. 5) in the body 2.

Figure 9:
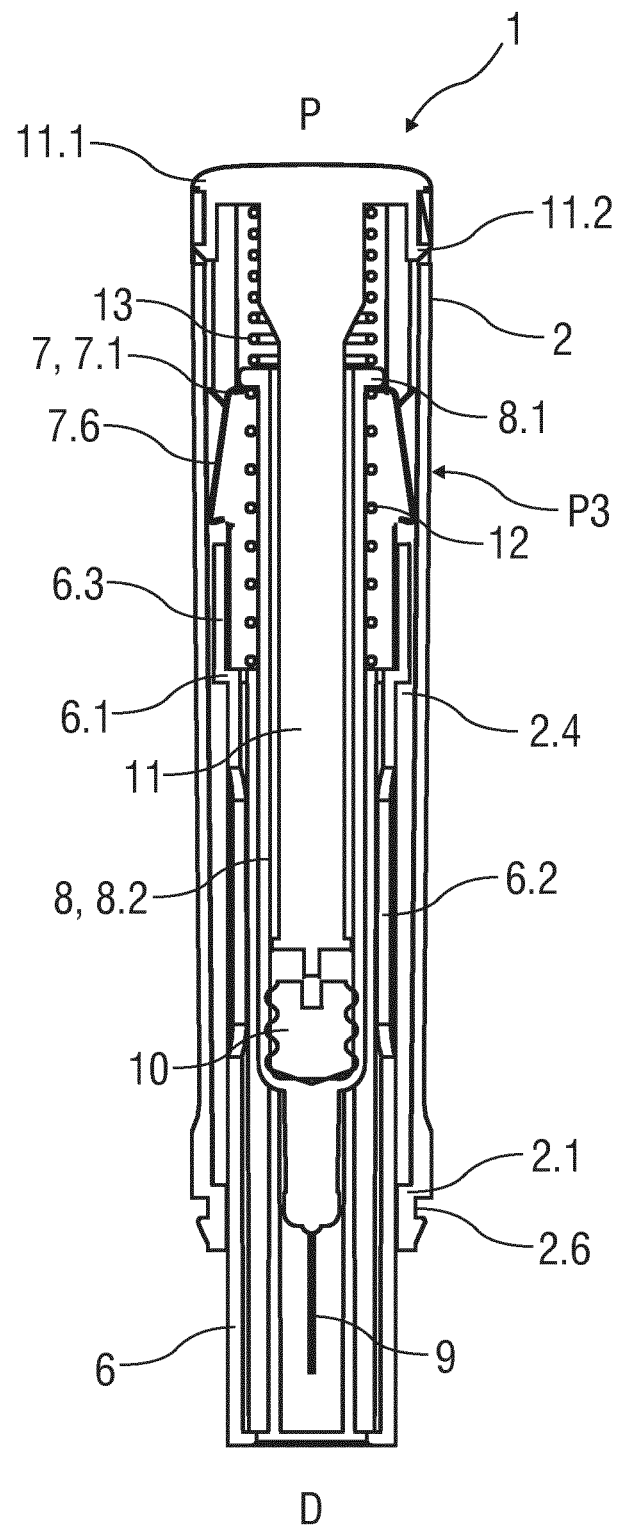
FIG. 9 is a schematic longitudinal section of an exemplary embodiment of a medicament delivery device after use.

One or more third legs 7.6 extend distally from the proximal portion 7.1. The third leg 7.6 is biased radially outward. The third leg 7.5 is adapted to engage one or more second ribs 2.4 (e.g., as shown in FIG. 9) in the body 2.

In an exemplary embodiment, the sleeve 6 comprises one or more sleeve legs 6.3 extending in the proximal direction P beyond the collar 6.1. The sleeve legs 6.3 are adapted to radially outwardly support the third legs 7.6 of the carrier 7 such that they cannot deflect radially outwards depending on the axial position of the sleeve 6 relative to the carrier 7, as explained below with regard to at least FIG. 8.

Referring again to FIG. 2, a piston rod 11 is arranged within the body 2 in a manner to engage the stopper 10 for displacing it within the syringe barrel 8.2. In an exemplary embodiment, the piston rod 11 is attached to the body 2, preventing relative movement between the piston rod 11 and the body 2. In an exemplary embodiment the piston rod 11 may be integrally shaped with the body 2, or in another exemplary embodiment, the piston rod 11 may be secured to the body 2 by latches 11.2 (shown in FIG. 4). In an exemplary embodiment, prior to use, an axial gap may be present between a distal end of the piston rod 11 and a proximal end of the stopper 10. The axial gap may prevent force being applied to the stopper 10 prior to use.

In an exemplary embodiment, a sleeve spring 12 is arranged between the carrier 7 and the sleeve 6 in a manner biasing the sleeve 6 in the distal direction D relative to the carrier 7 such that the collar 6.1 of the sleeve 6 abuts the first protrusion 7.3 of the carrier 7.

In an exemplary embodiment, a container spring 13 is arranged over the piston rod 11 between a proximal end face 11.1 of the piston rod 11 and the proximal flange 8.1 of the syringe 8 thus biasing the syringe 8 in the distal direction D relative to the piston rod 11 and body 2.

In an exemplary embodiment, a protective needle shield 14 is arranged over the needle 9. The cap 3 is adapted to engage (e.g., by a barb, hook, latch, etc.) the needle shield 14 in manner to remove it from the needle 9 once the cap 3 is removed from the body 2 by pulling it in the distal direction D. A snap feature 2.6 may be arranged on the body 2 for snap fitting the cap 3 to the body 2.

In order to perform an injection, the medicament delivery device 1 may be operated according to the following exemplary steps.

The cap 3 is pulled in the distal direction D relative to the body 2 thereby also pulling the protective needle shield 14 off the needle 9. The syringe 8 is prevented from moving in the distal direction D as its proximal flange 8.1 abuts the proximal portion 7.1 of the carrier 7, and the carrier 7 is prevented from moving in the distal direction D as the first leg 7.2 of the carrier 7 distally abuts a first axial stop 2.1 in the body 2. The collar 6.1 on the sleeve 6 distally abuts the first protrusion 7.3 on the first leg 7.2 such that the sleeve 6 is also prevented from moving in the distal direction D.

Figure 4:
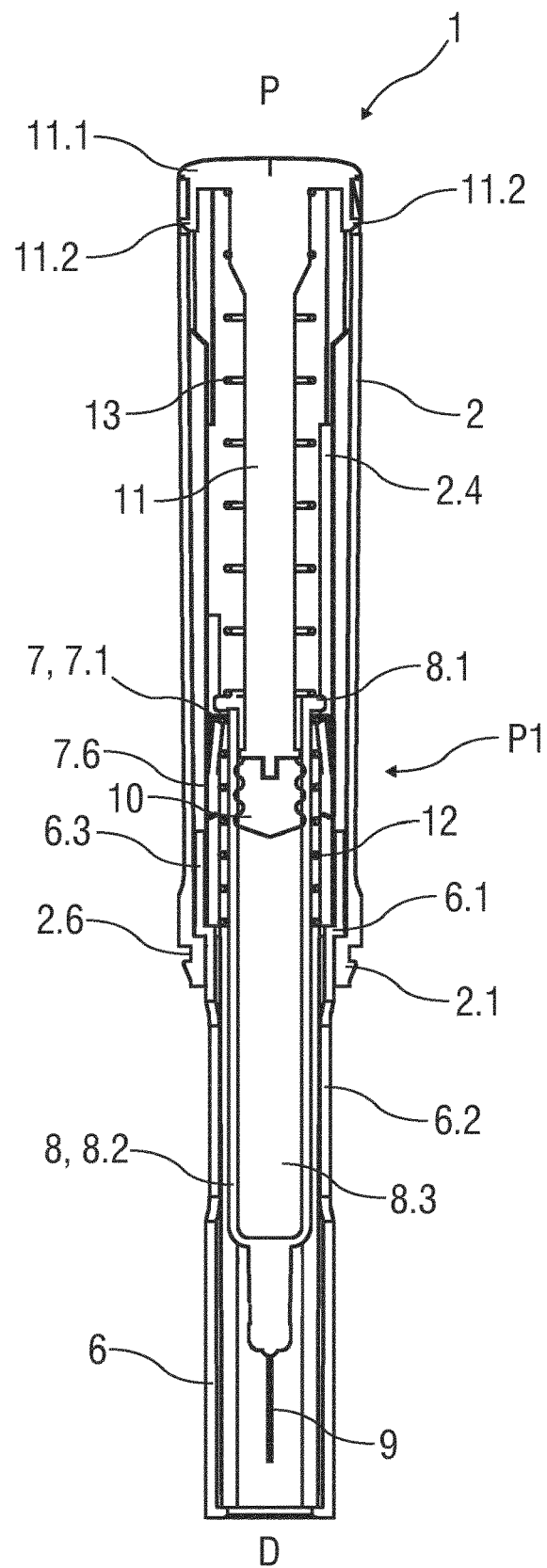
FIG. 4 is a schematic longitudinal section of an exemplary embodiment of a medicament delivery device prior to use.

FIG. 4 is a schematic longitudinal section of an exemplary embodiment of a medicament delivery device 1 according to the present disclosure prior to use. The needle 9 is located within the sleeve 6 preventing a user from touching and seeing it. In this state the medicament delivery device 1 may be held at the body 2 and the sleeve 6 may be pushed against an injection site, e.g. a patient's skin. Consequently the sleeve 6 moves in the proximal direction P relative to the body 2 against the force of both the sleeve spring 12 and the container spring 13. The sleeve spring 12 and the container spring 13 are selected such that a spring force of the sleeve spring 12 is less than a spring force of the container spring 13. Due to the movement of the sleeve 6 in the proximal direction P, the sleeve spring 12 will be compressed as the collar 6.1 of the sleeve 6 disengages the first protrusion 7.3 and moves towards the second protrusion 7.4, allowing the sleeve 6 to retract into the body 2. The carrier 7 and the syringe 8 remain in position (abutting the first axial stop 2.1) due to the force of the container spring 13. As the syringe 8 and the needle 9 stay in position relative to the body 2 while the sleeve 6 moves in the proximal direction P, a distal tip of the needle 9 is exposed beyond a distal end of the sleeve 6 and inserted into the injection site. Once the collar 6.1 abuts the second protrusion 7.4, movement of the sleeve 6 in the proximal direction P relative to the carrier 7 stops. The needle 9 has reached its insertion depth. Any further movement of the sleeve 6 relative to the body 2 in the proximal direction P causes the carrier 7 with the syringe 8 to move proximally relative to the body 2, because the collar 6.1 pushes the second protrusion 7.4. This proximal movement thus compresses the container spring 13. As the piston rod 11 is coupled to the body 2, this proximal movement causes the piston rod 11 to abut the stopper 10 and displace it within the syringe barrel 8.2 ejecting the medicament from the cavity 8.3 through the needle 9 into the injection site. A feedback may be provided to the user to indicate that dispensing of the medicament is being initiated. For example, a tactile feedback may be provided in the form of an increased resistance as the container spring 13 compresses.

Figure 7:
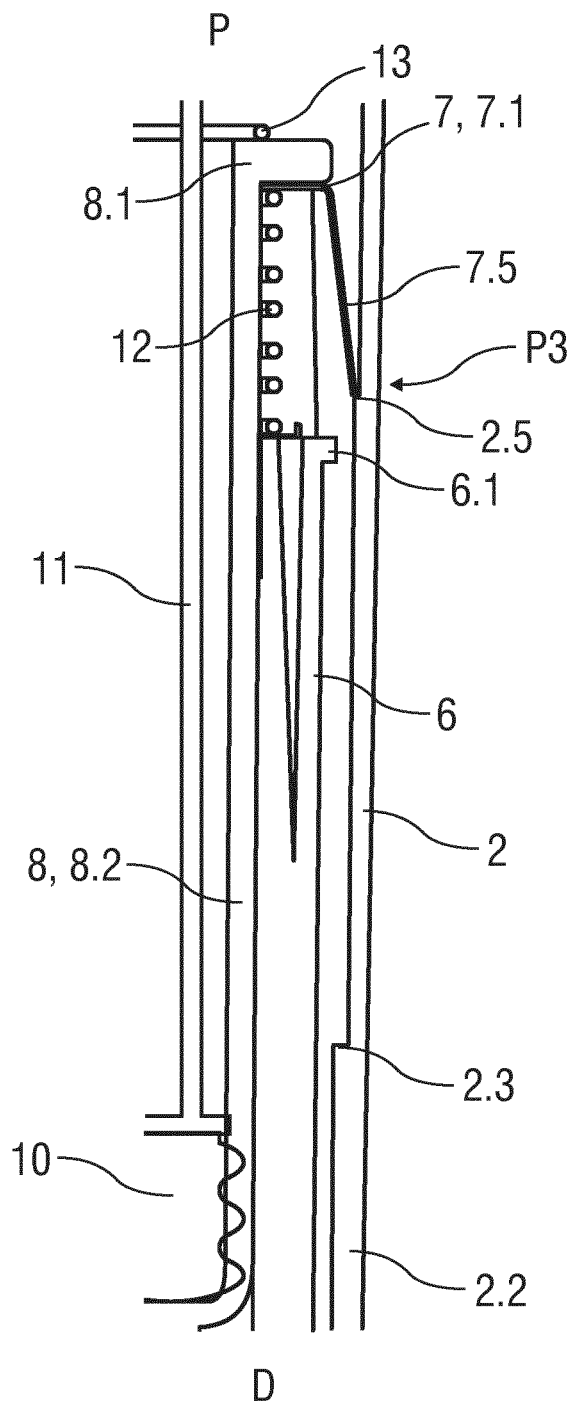
FIG. 7 is a longitudinal detail section of an exemplary embodiment of a medicament delivery device during use.

As shown in FIGS. 5 and 7, as the carrier 7 and the syringe 8 move proximally relative to the body 2, the second legs 7.5 are radially outwardly abutted by one or more first ribs 2.2. When the carrier 7 has travelled a sufficient proximal distance relative to the body 2, the second legs 7.5 deflect radially outward and may abut a second axial stop 2.3 on a proximal end of the first rib 2.2. Due to the second axial stop 2.3, the carrier 7 is prevented from moving in the distal direction D relative to the body 2. A third axial stop 2.5 may be disposed in the body 2 proximal of the second axial stop 2.3. When the second legs 7.5 proximally pass the third axial stop 2.5, the second legs 7.5 may deflect radially outward to abut the third axial stop 2.5 and prevent the carrier 7 from moving distally relative to the body 2. Those of skill in the art will understand that any number of axial stops may be formed in the body 2. Further, the axial stop may be formed as a rib with a transverse abutment surface or as a ramped surface with a transverse abutment surface. In an exemplary embodiment, a feedback (e.g., tactile and/or audible) may be provided when the carrier 7 proximally passes an axial stop. For example, when the second legs 7.5 deflect radially outward after proximally passing an axial stop, the second legs 7.5 may impact the body 2 generating a tactile feedback (e.g., a vibration) and/or an audible feedback (e.g., a 'click' sound). If the medicament delivery device 1 is removed from the injection site, the carrier 7 would travel in the distal direction D relative to the body 2 until the second legs 7.5 engage an axial stop, and the sleeve 6 would travel distally relative to the carrier 7 until the collar 6.1 abuts the first protrusion 7.3. Thus, the needle 9 would be covered again by the sleeve 6 despite the changed axial position of the carrier 7 and the syringe 8 relative to the body 2.

Figure 6:
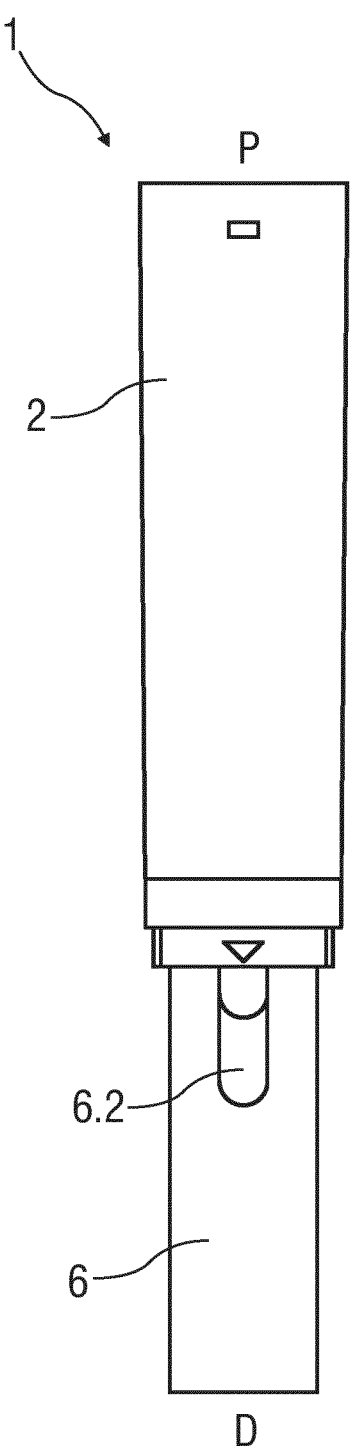
FIG. 6 is a schematic longitudinal section of an exemplary embodiment of a medicament delivery device during use.

FIG. 6 is a schematic view of the medicament delivery device 1 during use. An overall length of the medicament delivery device 1 is shorter than in an initial state, and the sleeve window 6.2 is partially hidden within the body 2 thus providing a visual indication that the medicament delivery device 1 has been used. If the medicament delivery device 1 is in this state, it can be re-applied against the injection site (or a different injection site) and the medicament delivery.

For example, a dose of a medicament may need to be administered in at two different injection sites. Thus, the medicament delivery device 1 could be used to administer a first partial dose at a first injection site. A feedback provided by the second legs 7.5 and an axial stop may indicate that the first partial dose is complete. The medicament delivery device 1 could then be relocated (with the distal tip of the needle 9 covered by the sleeve 6) to a second injection site to deliver a second partial dose. Due to the sleeve spring 12 being weaker than the container spring 13, the sleeve 6 will again move relative to the carrier 7 thus inserting the needle 9 into the injection site before the syringe 8 and carrier 7 move relative to the body 2 for delivering the medicament.

Figure 8:
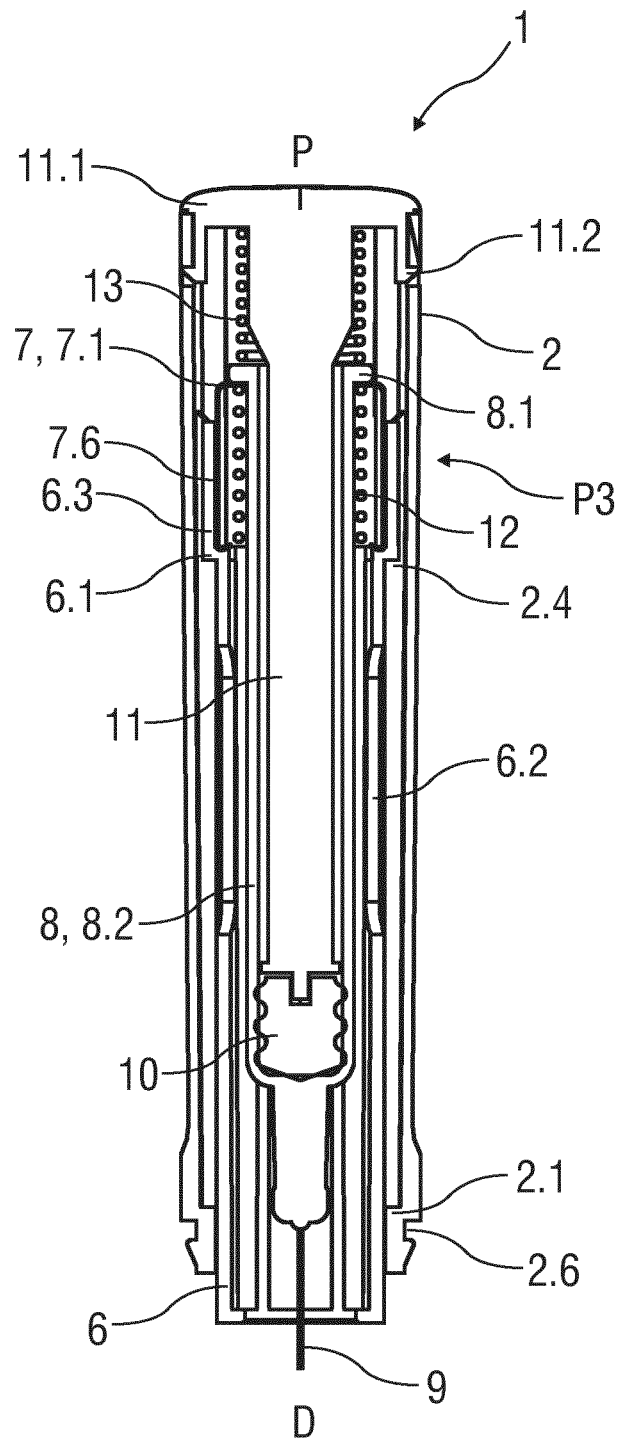
FIG. 8 is a schematic longitudinal section of an exemplary embodiment of a medicament delivery device during use.

As shown in FIG. 8, as the body 2 is pressed further against the injection site, the piston rod 11 will displace the stopper 10 until the stopper 10 bottoms out within the syringe 8 (or delivers the intended dose). At this point the force opposing the movement of the body 2 in the distal direction D relative to the sleeve 6 considerably increases providing a tactile feedback to indicate that the injection is finished. The second legs 7.5 may engage an axial stop (e.g., third axial stop 2.5) to prevent the carrier 7 from moving distally relative to the body 2.

As shown in FIG. 9, when the medicament delivery device 1 is removed from the injection site, the sleeve spring 12 returns the sleeve 6 in the distal direction D relative to the carrier 7 until the collar 6.1 abuts the first protrusion 7.3. As the sleeve 6 translates distally, the sleeve legs 6.3 disengage the third legs 7.6 of the carrier 7 allowing them to radially outwardly deflect. Due to the movement of the sleeve 6 relative to the carrier 7 the distal tip of the needle 9 is covered again by the sleeve 6. On an attempt to again move the sleeve 6 in the proximal direction P relative to the body 2, the sleeve legs 6.3 axially abut the outwardly deflected third legs 7.6 preventing re-exposure of the needle 9. The length of the second rib 2.4 can be modified in order to adapt the position and hence the percentage of medicament delivered at which the third legs 7.6 are allowed to deflect radially outwards and lock out the sleeve 6.

In an exemplary embodiment, the cap 3 of the medicament delivery device 1 serves for keeping the needle 9 sterile prior to use, for removing the protective needle shield 14, for preventing unintended use of the medicament delivery device 1 prior to removal of the cap 3 and for providing rigid packaging.

In an exemplary embodiment, the medicament delivery device 1 allows for application by a user, e.g. a patient or caregiver, wherein the body 2 can be held in one hand. The needle 9 of the medicament delivery device 1 is hidden from view during all states of operation.

In an exemplary embodiment, the insertion depth of the needle 9 is defined by the initial distance of the distal tip of the needle 9 from the distal end of the sleeve 6 and by the distance between the first protrusion 7.3 and the second protrusion 7.4 on the carrier 7 limiting relative axial movement of the sleeve 6.

In an exemplary embodiment, the forces required to insert the needle 9 into the injection site and to deliver the medicament can be adjusted by respectively selecting the sleeve spring 12 and the container spring 13, wherein the force for delivering the medicament depends on the container spring 13 and on the characteristics of the syringe 8, stopper 10, needle 9 and medicament.

Figure 10:
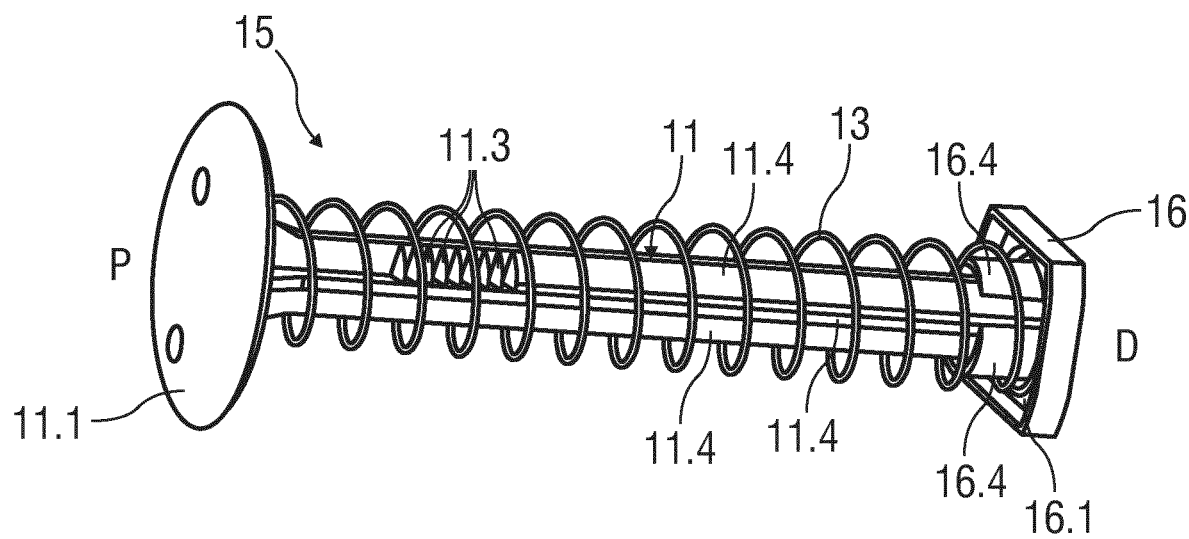
FIG. 10 is a schematic view of an exemplary embodiment of a feedback mechanism comprising a plunger and a bushing.
Figure 11:
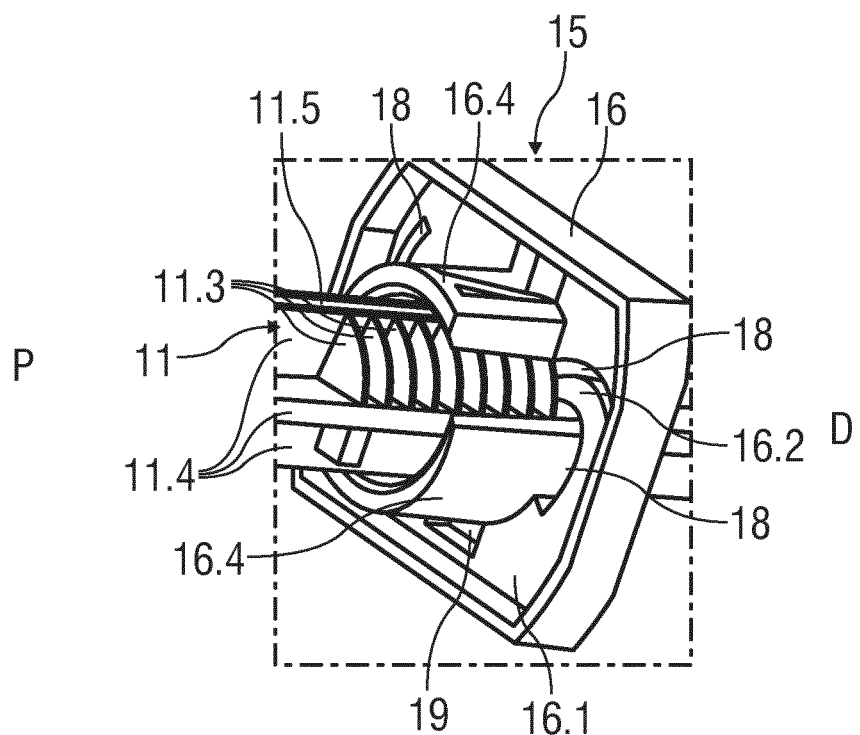
FIG. 11 is a schematic detail view of the feedback mechanism of FIG. 10.
Figure 12:
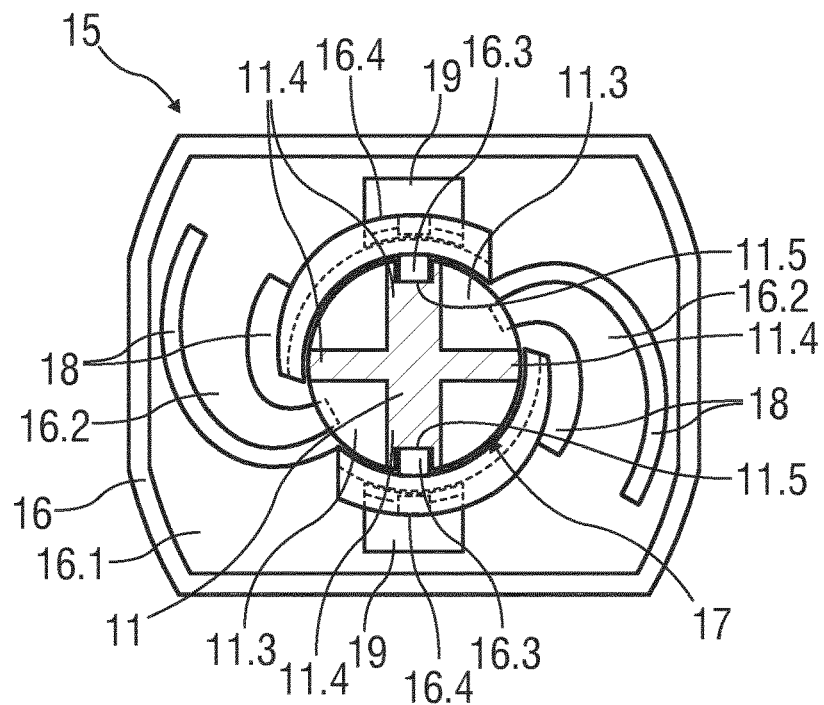
FIG. 12 is a schematic cross sectional detail view of the feedback mechanism.
Figure 13:
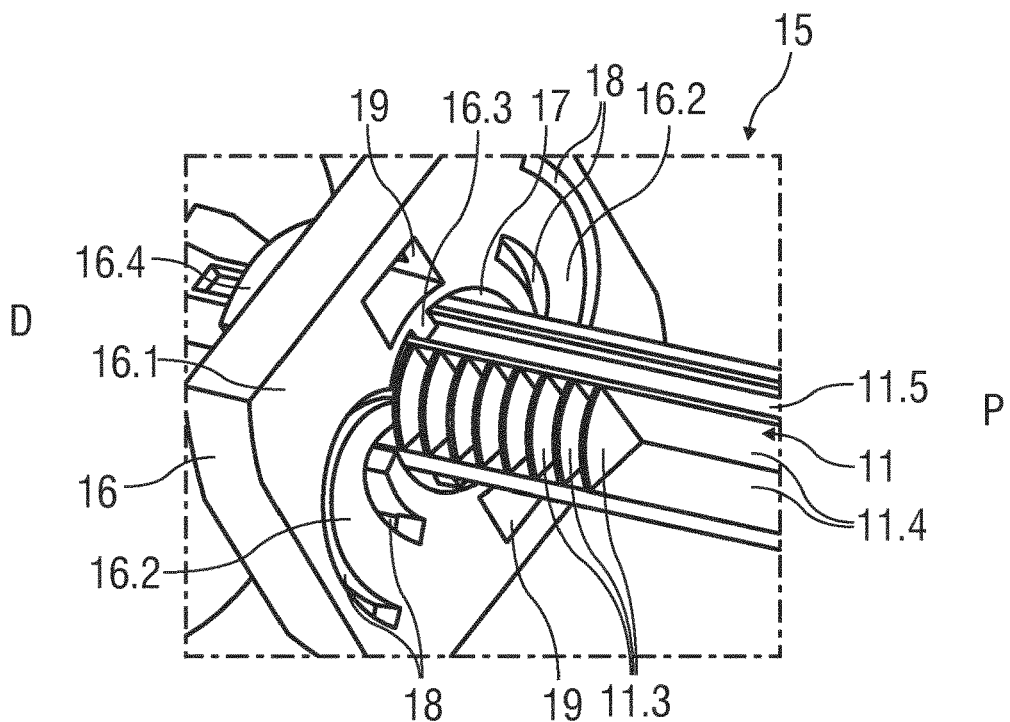
FIG. 13 is a schematic detail view of the feedback mechanism.
Figure 14:
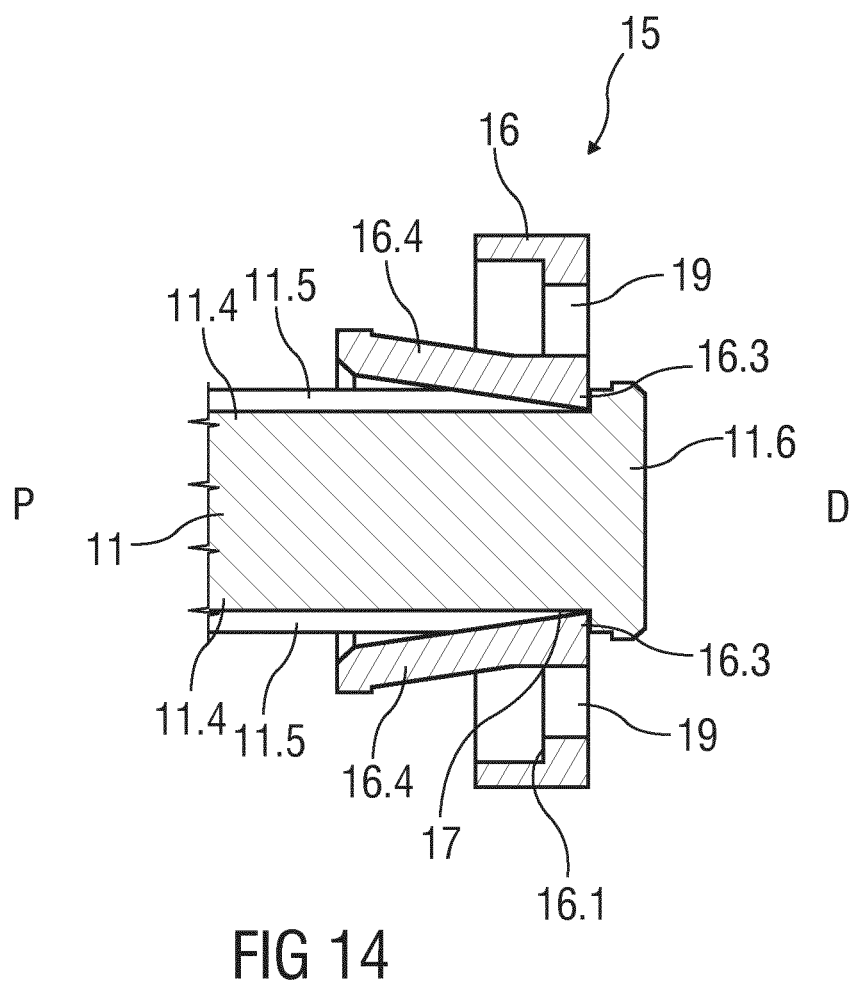
FIG. 14 is a schematic longitudinal sectional detail view of the feedback mechanism.

FIG. 10 is a schematic view of an exemplary embodiment of a feedback mechanism 15 comprising the piston rod 11 and a bushing 16. FIG. 11 is a schematic detail view of the feedback mechanism 15. FIG. 12 is a schematic cross sectional detail view of the feedback mechanism 15. FIG. 13 is another schematic detail view of the feedback mechanism 15. FIG. 14 is a schematic longitudinal sectional detail view of the feedback mechanism 15.

The bushing 16 comprises a central aperture 17 sized to slidably accommodate the piston rod 11 therein so that the bushing 16 may be arranged about the piston rod 11. A proximal surface of a transversal section 16.1 of the bushing 16 serves as a spring seat for the container spring 13. One or more resilient flaps 16.2 are provided on the bushing 16, the flaps 16.2 extending into the central aperture 17 to allow them to engage one or more, in particular two or more transversal ribs 11.3 arranged on at least part of the length of the piston rod 11.

In an exemplary embodiment, the piston rod 11 comprises a number of longitudinal webs 11.4 arranged at an angle relative to one another. The one or more transversal ribs 11.3 are arranged between at least two adjacent ones of these longitudinal webs 11.4. In an exemplary embodiment, the piston rod 11 comprises four longitudinal webs 11.4 arranged to form a substantially x-shaped cross section as best seen in FIG. 12. In an exemplary embodiment, an angular offset between two respectively adjacent longitudinal webs 11.4 is 90°.

In an exemplary embodiment, the flaps 16.2 are formed within the transversal section 16.1 by cut-outs 18 in the transversal section 16.1. In the illustrated embodiment, the flaps 16.2 are curved. In other, non-illustrated embodiments, the flaps 16.2 may be straight.

In an exemplary embodiment, the bushing 16 comprises one or more spline features adapted to engage corresponding spline features in the piston rod 11 to restrain or prevent relative rotation between the piston rod 11 and the bushing 16. In an exemplary embodiment, the spline features comprise one or more radially inward directed protrusions 16.3 on the bushing 16 adapted to engage longitudinal slots 11.5 in one or more of the longitudinal webs 11.4. In other embodiments, the protrusions 16.3 could engage between two adjacent ones of the longitudinal webs 11.4.

In an exemplary embodiment, the piston rod 11 comprises a distal end face 11.6 providing an axial stop for the protrusions 16.3 so as to limit movement of the piston rod 11 in the proximal direction P relative to the bushing 16. This may be achieved by the longitudinal slots 11.5 ending at the distal end face 11.6 and not extending through it. The axial stop also serves as a fixation for the container spring 13 to fix it in a pre-load position.

In an exemplary embodiment, the protrusion 16.3 is arranged in the transversal section 16.1 and a recess 19 is provided radially outward of the protrusion 16.3 in the transversal section 16.1. The protrusion 16.3 may be inclined outward in the proximal direction P allowing insertion of the distal end face 11.6 of the piston rod 11 through the central aperture 17 in the distal direction D thereby deflecting the protrusion 16.3 radially outwards. The deflection is facilitated by the recess 19. Once the distal end face 11.6 has passed beyond the protrusion 16.3 during this insertion movement, the protrusion 16.3 relaxes, engages the longitudinal slot 11.5 and prevents the distal end face 11.6 from being moved back out of the central aperture 17 in the proximal direction P.

The bushing 16 may comprise one or more proximal beams 16.4 extending from the transversal section 16.1 in the proximal direction P. The proximal beams 16.4 may be integrally formed with the transversal section 16.1. In an exemplary embodiment, the protrusion 16.3 is arranged on an intersection of the proximal beam 16.4 with the transversal section 16.1. In a relaxed state, the proximal beam 16.4 may be inclined outward in the proximal direction P providing a lead-in for the distal end face 11.6 of the piston rod 11 for inserting the piston rod 11 through the central aperture 17 in the distal direction D. The proximal beam 16.4 may have an arcuate cross section; e.g. the proximal beam 16.4 may be formed as a sector of a hollow cylinder or a hollow cone.

The piston rod 11 may comprise a plurality of transversal ribs 11.3 arranged in a sequence.

During an injection stroke, the syringe 8 moves proximally relative to the piston rod 11 and the syringe 8, in particular the proximal flange 8.1 of the syringe 8, abuts the bushing 16 so that the bushing 16 is moved in the proximal direction P along the piston rod 11. During this movement, the flap 16.2 abuts one of the transversal ribs 11.3 and is deflected by the transversal rib 11.3 upon further movement until the flap 16.2 disengages the transversal rib 11.3 and relaxes thereby hitting a subsequent transversal rib 11.3 generating a click sound. By arranging a plurality of ribs 11.3 in a sequence, a series of clicks can thus be generated during the injection stroke.

The number and positions of the transversal ribs 11.3 may be adjusted so as to generate clicks only at predetermined points during the injection stroke, e.g. at an end of dose. For an end of dose indication, it may be sufficient to provide only two transversal ribs 11.3. In an exemplary embodiment, more than two transversal ribs 11.3 may be provided for the end of dose indication thus allowing compensating tolerances within the drug delivery device 1. In other embodiments, the transversal ribs 11.3 may be arranged at different positions to indicate a start of the injection or one or more predetermined partial doses. In another embodiment, the transversal ribs 11.3 may be arranged over the whole length of the piston rod 11 thus indicating an injection progress.

The feedback mechanism 15 may be applied with the drug delivery device 1 illustrated in FIGS. 1 to 9. In this case, the bushing 16 is arranged on the piston rod 11 and not attached to the body 2 allowing the bushing 16 to be moved relative to the piston rod 11 during the injection stroke when abutted by the syringe 8.

The feedback mechanism 15 may likewise be applied with other, not shown drug delivery devices 1. For example, a drug delivery device 1 may have a piston rod 11 movable relative to the body 2. In this case, the bushing 16 may be axially fixed within the body 2.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

REFERENCE NUMERALS 1 drug delivery device
2 body
2.1 first axial stop
2.2 first rib
2.3 second axial stop
2.4 second rib
2.5 third axial stop
3 cap
4 viewing window
5 indicia
6 sleeve
6.1 collar
6.2 sleeve window
6.3 sleeve leg
7 carrier
7.1 proximal portion
7.2 first leg
7.3 first protrusion
7.4 second protrusion
7.5 second leg
7.6 third legs
8 syringe
8.1 proximal flange
8.2 syringe barrel
8.3 cavity
9 needle
10 stopper 11 piston rod
11.1 proximal end face
11.2 latch
11.3 transversal rib
11.4 longitudinal web
11.5 longitudinal slot
11.6 distal end face
12 sleeve spring
13 container spring
14 protective needle shield
15 feedback mechanism
16 bushing
16.1 transversal section
16.2 flap
16.3 protrusion
16.4 proximal beam
17 central aperture
18 cut-out
19 recess
D distal direction
P proximal direction

The invention claimed is:

1. A feedback mechanism for a drug delivery device, the feedback mechanism comprising a bushing, the bushing comprising a central aperture adapted to accommodate a piston rod, wherein one or more resilient flaps are provided on the bushing, the flaps extending into the central aperture to allow the flaps to engage one or more transversal ribs on the piston rod, wherein the bushing comprises one or more spline features adapted to engage corresponding spline features in the piston rod, to one or both of restrain or prevent relative rotation between the piston rod and the bushing.

2. The feedback mechanism according to claim 1, wherein the flaps are formed within a transversal section of the bushing by cut-outs in the transversal section.

3. The feedback mechanism according to claim 1, wherein the flaps are curved.

4. The feedback mechanism according to claim 2, wherein the spline features comprise one or more radially inward directed protrusions on the bushing the one or more protrusions adapted to engage longitudinal slots in at least one longitudinal web of the piston rod.

5. The feedback mechanism according to claim 4, wherein the one or more protrusions are arranged in the transversal section, and wherein a recess is provided radially outward of the protrusion in the transversal section.

6. The feedback mechanism according to claim 5, wherein the bushing comprises one or more proximal beams extending from the transversal section in a proximal direction, wherein the one or more protrusions are arranged on an intersection of the one or more proximal beams with the transversal section, wherein when the one or more proximal beams are in a relaxed state, the one or more proximal beams are inclined outward in the proximal direction and provide a lead-in for a distal end face of the piston rod.

7. The feedback mechanism according to claim 6, wherein the one or more proximal beams are integrally formed with the transversal section.

8. The feedback mechanism according to claim 6, wherein at least one of the one or more proximal beams has an arcuate cross section.

9. The feedback mechanism according to claim 1, wherein two or more transversal ribs are provided on the piston rod.

10. The feedback mechanism according to claim 1, wherein the piston rod comprises a number of longitudinal webs arranged at an angle relative to one another, wherein the one or more transversal ribs are arranged between at least two adjacent ones of the longitudinal webs arranged at the angle.

11. The feedback mechanism according to claim 6, wherein the distal end face of the piston rod is arranged as an axial stop for the one or more protrusions and limits movement of the piston rod in the proximal direction relative to the bushing.

12. A drug delivery device comprising:
a body,
a piston rod arranged in the body, the piston rod configured to engage a stopper for displacing the stopper within a syringe barrel of a syringe,
a feedback mechanism for the drug delivery device, the feedback mechanism comprising a bushing, the bushing comprising a central aperture adapted to accommodate a piston rod, wherein one or more resilient flaps are provided on the bushing, the flaps extending into the central aperture to allow the flaps to engage one or more transversal ribs on the piston rod, wherein the bushing comprises one or more spline features adapted to engage corresponding spline features in the piston rod, to one or both of restrain or prevent relative rotation between the piston rod and the bushing, wherein the bushing is adapted to engage the syringe during movement of the piston rod relative to the syringe and cause movement of the bushing relative to the piston rod.

13. The drug delivery device according to claim 12, wherein a number and position of the transversal ribs are selected such that one or more of: i) at least one click is generated by engaging the one or more protrusions at an end of dose, ii) a start of the injection is indicated, or iii) an end of one or more predetermined partial doses is indicated.

14. The drug delivery device according to claim 12, further comprising a container spring arranged over the piston rod between a proximal end face of the piston rod and a transversal section of the bushing.

* * * * *